United States Patent [19]

Apontoweil et al.

[11] Patent Number: 4,537,768

[45] Date of Patent: Aug. 27, 1985

[54] COMBINED VACCINE

[75] Inventors: Peter Apontoweil, EK Leersum; Johannes A. G. Kok, AB Soest, both of Netherlands

[73] Assignee: Roussel Uclaf, Paris, France

[21] Appl. No.: 356,952

[22] Filed: Mar. 11, 1982

Related U.S. Application Data

[63] Continuation of Ser. No. 73,431, Sep. 7, 1979, abandoned.

[30] Foreign Application Priority Data

Sep. 14, 1978 [NL] Netherlands ............ 7809364
Apr. 26, 1979 [NL] Netherlands ............ 7903300

[51] Int. Cl.³ .................... A61K 39/17; A61K 39/235
[52] U.S. Cl. .................................. 424/89; 424/88
[58] Field of Search ............... 424/89; 435/235, 237, 435/238, 239

[56] References Cited

U.S. PATENT DOCUMENTS

| 3,060,094 | 10/1962 | Dutcher et al. | 424/89 |
| 3,083,142 | 3/1963 | Howell et al. | 424/89 |
| 3,149,036 | 9/1964 | Woodhour et al. | 424/89 |
| 3,399,263 | 8/1968 | Strazdins et al. | 424/89 |
| 3,678,149 | 7/1972 | Prigal | 424/89 |
| 3,755,557 | 8/1973 | Jacobs | 424/89 |
| 3,876,763 | 4/1975 | Yoshikazu et al. | 424/89 |
| 3,906,092 | 9/1975 | Hilleman et al. | 424/89 |
| 3,983,228 | 9/1976 | Woodhour et al. | 424/89 |
| 4,069,313 | 1/1978 | Woodhour et al. | 424/89 |
| 4,073,743 | 2/1978 | Midler et al. | 424/89 |

FOREIGN PATENT DOCUMENTS

| 277937 | 11/1965 | Australia | 424/89 |
| 2382500 | 9/1978 | France | . |
| 48-72317 | 9/1973 | Japan | 424/89 |
| 50-6714 | 1/1975 | Japan | 424/89 |
| 52-9727 | 3/1977 | Japan | 424/89 |
| 292949 | 7/1965 | Netherlands | 424/89 |

OTHER PUBLICATIONS

Veterinary Bulletin 47, #1481, #6897 (1977), 48, #2966, #2971, #4417, #5414, #5417, #5421, #7257 (1978).

*Primary Examiner*—Shep K. Rose
*Attorney, Agent, or Firm*—Charles A. Muserlian

[57] ABSTRACT

Combined, inactivated vaccine ready for administration and active against at least Newcastle disease and egg production drop caused by adeno-like viruses and process for the preparation of such vaccine by addition of (A) a Newcastle disease virus (NDV) containing liquid obtained by cultivation of a NDV, followed by inactivation of the liquid and optionally homogenizing it, together with (B) an adeno-like virus (ALV) containing liquid obtained by cultivation of an ALV, followed by inactivation of the liquid and optionally homogenizing it, to an oil phase containing as essential components at least one of the components selected from the group consisting of light paraffinic mineral oils, vegetable oils and naphtenic mineral oils and one or more emulsifiers such as nonionic surface-active compounds derived from alkylene oxide and/or hexahydric alcohols and/or higher natural fatty acids such as esters or ester-ethers, optionally followed by homogenizing and/or addition of a preservative.

14 Claims, 1 Drawing Figure

NDV
HAI UNITS ----
$2^X$

ADENO 127
HAI LEVEL $2^X$ ___

(graph: y-axis 0–20, x-axis 2–14 WEEKS P.V.)

COMBINED VACCINE

PRIOR APPLICATIONS

This application is a continuation of our copending, commonly assigned U.S. patent application Ser. No. 73,431 filed Sept. 7, 1979 now abandoned.

Newcastle disease [abbreviated ND], one of the most important respiration diseases in poultry, is caused by a virus, and may cause a high mortality in poultry of all ages. Several vaccines against Newcastle disease have been developed, and it has turned out that those vaccines are preferably administered in their inactivated form since that form provides a high degree of safety. In addition, the use of a live vaccine sometimes results in the inoculated virus being distributed from vaccinated poultry to poultry susceptible to infections or which are not immune. Although various relatively safe and well immunizing, live ND vaccines have been developed, as e.g. appears from British Patent Specification No. 1,510,100, there is still a clear need for inactivated ND vaccines.

Since respiration diseases in poultry are often the result of more than one infection source, combined vaccines have been developed, for example that of U.S. Pat. No. 2,798,835 which consists of a combination of a vaccine against infectious bronchitis and an ND vaccine, both components being derived from live viruses. Furthermore, published Dutch patent application No. 7117873 discloses a process for the preparation of a combined vaccine against respiration diseases in poultry characterized by combination of a dead vaccine against infectious coryza obtained by cultivating a Haemophilus gallinarium strain in a natural nutrient medium and subsequently inactivating the bacteria, with a dead vaccine from an infectious bronchitis virus and a dead ND vaccine. Several references, e.g. Avian Dis. 7 (1963) pages 106 to 122, Am. J. Vet. Res. 17 (1956) pages 294 and 298, Avian Dis. 11 (1967) pages 399 to 406 and Virology 33 (1967) pages 598 to 608, disclose that the activity of each of the components may decrease or may be lost entirely by mixing live viruses caused, by mutual inhibition.

A connection between the presence of adeno-like viruses (hereinafter indicated ALV) and, in part, the sudden drop in egg production and/or increasing production of eggs with soft shells and/or without shells, observed increasingly in the past years, particularly in broiler mother animals and chickens of medium heavy lay races, is already indicated in Avian Pathology 5 (1976) pages 261 to 272. The literature calls such symptoms sometimes "egg drop syndrome". Avian Pathology, 6 (1977), pages 405 to 413 also discloses a relation observed between the development of antibodies with regard to a hemagglutinizing virus, called 127 virus, and the economically very disadvantageous symptoms described hereinabove. Avian Pathology (1978), pages 35 to 47 confirms the assumed relation between the presence of an adeno-like virus and the sudden drop in production described hereinabove. In addition, several characteristic properties of the type of virus in question are described, e.g. the characteristic agglutination of chicken erythrocytes and the incapability of antisera of being neutralized in the known adeno virus types.

Luxembourg Pat. No. 79,154 discloses a process for the preparation of a vaccine against the "egg drop syndrome", starting from an ALV characterized by a specific hemagglutination and antisera reaction. In the description and the examples, this virus is called EDS-76 and BC-14. The vaccine was prepared by cultivating the new virus in a tissue culture, preferably in an avian tissue culture such as chicken embryo fibroblasts and embryonal liver or kidney cells or in embryonated duck eggs. From Avian Pathology 5 (1976), page 262, second paragraph, from Avian Pathology 6 (1977), page 406 and from Luxembourg Pat. No. 79,154, page 1, lines 7 to 11 as well, it is evident that an egg production drop may be caused by Newcastle disease, infectious bronchitis, avian and cefalomyelitis, birdpox viruses and combinations thereof.

Therefore, from a practical point of view, poultry will often simultaneously or a short time after each other be vaccinated with two or more vaccines against the abovementioned, more generally occurring virus diseases. Particularly, poultry will simultaneously be vaccinated against Newcastle disease and production drop caused by ALV as well. The hitherto usual method for any such simultaneous administration consisted of mixing standard volumes of the separate vaccines ready for use and the administration of a vaccine dose prepared in the spot, with the administration consisting therefore of substantially double the volume as compared to those of separately administered vaccines with the respective virus amounts being diluted. Moreover, an exact mixing can hardly be guaranteed, and problems due to foreign infectious matter may arise.

OBJECTS OF THE INVENTION

It is an object of the invention to find a combined, ready for use vaccine effective against Newcastle disease and egg production drop caused by ALV as well which meets the present severe requirements of veterinary authorities in most of the relevant countries.

It is another object of the invention to provide a novel process for the combined vaccine and novel viruses.

It is additional object of the invention to provide a novel method of simultaneously immunizing chickens against Newcastle disease and egg production drop.

These and other objects and advantages of the invention will become obvious from the following detailed description.

THE INVENTION

The novel combined, ready for use vaccine of the invention is comprised of an inactivated Newcastle disease virus containing aqueous liquid and an inactivated adeno-like virus containing aqueous liquid in an oil phase optionally containing other virus types. Preferably, the volume ratio of Newcastle disease virus to adeno-like virus is 3:4 to 5:1, preferably 3:2.

For the process of the invention, the inactivated NDV-containing liquid is prepared in a manner known per se in principle, e.g. by cultivating the desired virus in fertilized chicken eggs, collecting the cultivated virus in a liquid of a titre usual for this kind of vaccine, inactivating it, suspending the virus in a suitable buffered solution, homogenizing the suspension, mixing it with an inactivated virus liquid derived from an ALV prepared by cultivating the virus in fertilized duck eggs or in a cell culture of duck's cells, collecting the virus produced in a liquid having a titre usual for this type of vaccine and inactivating the virus liquid according to methods known per se.

For the preparation of the NDV-containing liquid, various slightly virulent or practically avirulent (lentogenic or velogenic) ND viruses having good immunizing properties may be used such as the La Sota or Hitchner virus (lentogenic) or the Herts 33/56 (velogenic) virus. Specific examples of applicable virus strains, are the strains P/76/5, P/76/4 and P/76/3 obtainable from Institut für Medizinische Mikrobiologie, Infections und Seuchenmedizin der Ludwig Maximilians Universität, München, the VR-108, VR-107, VR-109, VR-669, VR-623 strains obtainable from the American Type Culture Collection, Rockville, Md., USA, the Queensland V 4 strain obtainable from the Centr. Vet. Labs., Weybridge, Great Britain or the L/Z 258 P virus deposited with the Collection d'Institut Pasteur, Paris under I.091.

For the preparation of the inactivated ALV liquid component, a passaged virus strain 127 deposited with the Collection d'Institut Pasteur, Paris under No. I.090 is preferably used, although also other, with rather similar antigenicity, egg drop causing ALV virus types may be successfully used. The virus strain I.090 is preferably cultivated in duck eggs. The preparation of the inactivated ALV liquid is preferably started from a virus derived from a passaged virus strain 127 as indicated in the Avian Pathology references cited hereinabove, although other egg production drop causing ALV types may be successfully used too.

For the preparation of the combined vaccine, 150 to 250 ml of a buffered NDV-containing liquid is inactivated, is optionally homogenized and, together with 100 to 200 ml of a buffered previously inactivated ALV-containing liquid and optionally homogenized, are added to 600 to 700 ml of an oil phase. The essential components of the oil phase are at least one of the components selected from the group consisting of light paraffinic mineral oils (FDA quality), vegetable oils, and naphthenic mineral oils, together with at least one suitable emulsifier such as nonionic surface-active compounds derived from alkylene oxide and/or hexahydric alcohols and/or higher natural fatty acids ($C_{10}$ to $C_{20}$), e.g. esters and ester-ethers. Examples thereof are mannide monooleate (Span 80, Arlacel 80, Arlacel A) and polyoxyethylene (20) sorbitan monooleate (e.g. Tween 80).

The volume ratio of the buffered NDV-containing liquid and the buffered ALV-containing liquid may vary from 3:4 to 5:1 and is preferably about 3:2. The volume ratio of the aqueous phase formed by both virus liquids and the oil phase may vary from 1:1 to 3:7 and is preferably about 7:13. It has been found that the aqueous phase must be added to the oil phase under vigorous stirring and/or homogenizing to obtain the desired stable and thin liquid final emulsion.

The oil phase contains 2 to 20% by weight (based on the oil phase weight) of an emulsifier, preferably 2 to 15% by weight of Arlacel A or Arlacel 80 or Span 80 and 0.2 to 4% of Tweens 80. The components of the oil phase are preferably separately heated to at least 110° C. in an autoclave or sterile filtered as a mixture.

The inactivation of both starting virus liquid components may be performed with the usual inactivators, e.g. by means of β-propiolacetone, optionally combined with a stabilizer, or formaldehyde. Preferably β-propiolacetone is added in a concentration of 0.05 to 0.25% by weight (based on the aqueous phase weight) to a buffered ND virus-containing liquid and the liquid is incubated at about 37° C. for 1 to 2 hours, preferably 90 minutes, while the buffered ALV liquid is inactivated with formaldehyde and preferably at about 20° C. for about 20 hours in a concentration of 0.02 to 0.5% by weight. Then, if necessary, the virus liquids are homogenized in the usual manner. A preservative such as thiomersal or formaline in a buffered solution may then optionally be added to the aqueous phase.

To obtain the combined vaccine giving rise to the desired favorable titers after administration, NDV starting solution of a titre of $10^{9.8}$ EID 50/ml to $10^{10.5}$ EID 50/ml and preferably $\geq 10^{10}$ EID 50/ml is used and an ALV liquid with an activity of at least $10^2$ HA units, and preferably $10^3$ HA units is used.

It will be clear that the favorable properties of the combined virus vaccines could not have been predicted at all by a person skilled in the art since, due to several undesired reactions which certainly could not excluded by skilled people, the activities of one or both virus components in the final vaccine could have decreased to an undesired level caused by undesired mutual interactions between the virus liquid components or by interactions of these liquid components with one of the applied auxiliary chemicals. For example, one skilled in the art would certainly not exclude that the added β-propiolacetone would inactivate one of the virus components too strong by acting for a too long period, while such period is necessary for the inactivation of the other component.

The use of the combined vaccine of the invention is advantageous with respect to the prior art vaccines prepared by mixing of the component vaccines at the time of use in that a smaller volume (e.g. 0.5 cm$^3$ instead of 1 cm$^3$) is necessary for administration thus causing less local irritation. Moreover, a smaller amount of chemicals foreign to the body are administered. Furthermore, problems mentioned hereinabove caused by mixing and introduction of foreign infectious matter are avoided.

The thus prepared vaccines are usually administered to 10 to 20 weeks old birds before the lay at the effective dose.

The invention further relates to a process for preparing a suitable ALV-containing starting liquid which comprises cultivating an adeno-like virus in duck eggs or on a culture of duck embryo fibroblasts e.g. a monolayer rolling bottle culture or a culture of cells attached to solid inert carriers.

According to a preferred embodiment of the invention, a monolayer rolling bottle culture of duck's embryo fibroblasts is formed by suspending the starting cells in a culture medium consisting of at least 70 to 90 parts of Eagle's medium and optionally 5 to 15 parts of calf serum, a 2 to 4% sodium bicarbonate solution and 1 to 5 parts of a solution or a suspension of one or more antibiotics such as penicillin G, streptomycin and natamycin, and the culture liquid is separated when the cell culture is nearly closed. The cell culture is infected with virus suspension at 37° C. for 0.5 to 2 hours to attach the virus and is followed by addition of maintenance medium consisting of Eagle's medium with 2 to 10% of calf serum, 2–10 parts of tryptose broth (30 g/l), 10–20 parts bovine amnion fluid, and the additives indicated herebefore, and harvesting the virus-containing medium and cells 0.5 to 2 days after the CPE appearance.

The cell culture is inoculated with an ALV suspension having an activity of $\geq 30 \times 10^6$ TCID 50/rolling cuture bottle. In this connection, it has been found that cell suspension cultures were not suitable for the process discussed herebefore.

For the vaccine preparation, a passaged virus strain 127 deposited with the Collection d'Institut Pasteur, Paris under No. I.090, is preferably used and this strain is preferably cultivated in duck eggs.

It is true that Luxembourg Pat. No. 79,154 generally discloses the preparation of vaccines against "egg drop syndrome", but the presently proposed preferred production method on a commercial scale for these vaccine liquids of acceptable high titers is not described in any way or even suggested. In this connection, it is indicated on page 2, lines 28 to 30 of the said Luxembourg Patent clearly that the virus, i.a. may be cultivated on chicken embryo fibroblasts. However, it has been found that such method certainly does not lead to the desired, economically required results. Page 6, lines 29 to 35 disclose that a culture of embryonal chicken liver cells is used which however doesn't lead to the desired economically required results either, since cultivation on a commercial scale of embryonal liver cells is still considered a very difficult and thus expensive production method.

In the following examples there are described several preferred embodiments to illustrate the invention. However, it should be understood that the invention is not intended to be limited to the specific embodiments.

EXAMPLE 1

STEP A: Cultivation of adeno-like virus (passaged strain 127)

In Bellco rolling culture bottles, cell cultures of DEF were made from duck's eggs which are brooded for 12 to 13 days in Eagle 10% calf serum medium containing 0.22% by weight of $NaHCO_3$ and 2% by volume of an antibiotic solution containing penicillin G, streptocycin and natamycin. The medium was removed by vacuum when the cell cultures were nearly closed. Then the cultures were inoculated with a suspension of the passaged virus 127 strain, incubated at 37° C. for 1 hour and filled up with Eagle's maintenance medium containing 5% of calf serum, 10% by volume of tryptose phosphate broth (30 g/l), 0.22% by weight of $NaHCO_3$ and 2% by volume of the abovementioned antibiotic solution. The ALV-containing medium and the cells were harvested one day after a CPE appearance and the cells nearly coming off the glass wall. The virus suspension was frozen at $-20°$ C. and was stored for vaccine production. The HA titre and the $TCID_{50}$ of this suspension were estimated.

STEP B: Cultivation of NDV

SPF eggs, which were brooded for 11 days, were inoculated with L/Z 258 P virus and the culture was incubated at 37° C. for 72 hours and the AAF (Amnion Allantoic Fluid) was harvested. The AAF contained then about $10^{10} EID_{50}/ml$. The virus suspension was frozen at $-20°$ C. or lower and was stored for vaccine production.

SPF eggs, which were brooded for 11 days, were inoculated with Hertz 33/56 seed virus and after incubation at 37° C. for 24 to 48 hours, the AAF was harvested and contained then about $10^{10} EID_{50}/ml$. The virus suspension was frozen at $-20°$ C. or lower and was stored for vaccine production.

STEP C: Treatment of virus suspension

The frozen virus suspension were defrosted and inactivated with 0.05 to 0.25% of $\beta$-propiolactone in a water bath at 37° C. from 90 minutes and the suspensions were stored overnight at $+4°$ C. The inactivation was controlled by observing CPE's on DEF or CEF followed by a hemabsorption test. Moreover previously brooded SPF chicken eggs are incubated with the inactivated virus fluid and subsequently controlled. The virus suspensions were homogenized with an Ultra Turrax homogenizer. If desired, the suspension was diluted with PBS+0.3% of formaline, depending on the $EID_{50}$ of the AAF and HA titre of the adeno-like virus suspension. The NDV-AAF and the adeno-like virus suspension were mixed thereafter in a ratio of 6:4 and used for emulsion preparation.

STEP D: Preparation of the emulsion

The virus suspensions were mixed with the oil phase in a ratio of 6.5 parts of oil to 3.5 parts of virus liquid and emulgated in such a way that the average drop size of the aqueous phase was about $0.05-0.5\mu$ e.g. by injection of the virus suspension into the oil phase with simultaneous homogenizing with an Ultra Turrax homogenizer.

The oily phase is composed of 93.6% by volume of Marcol 52 (white paraffinic Esso oil) and 6.0% by volume of Arlacel A or Arlacel 80 or Span 80 (mannide monooleate) and 0.4% by volume of Tween 80 (polyoxyethylene-20-sorbitan monooleate). The components of the oil phase were separately heated to 110° C. in an autoclave or sterile filtered as a mixture.

A stable emulsion was obtained tested by (1) pipetting directly after emulsifying drops of emulsion onto an aqueous surface, whereby the drops did not spread out but remained intact; (2) allowing to stand at 37° C. for 4 weeks whereby an aqueous phase did not separate. The final concentrations of the thus prepared emulsions were 21% NDV containing buffered liquid and 14% ALV 127 containing, buffered liquid.

The vaccine obtained was used in a dosage of 0.5 ml per animal intramuscularly in the breast or leg muscles or subcutaneously in the neck. Eight days after vaccination, hemagglutination inhibiting anti-compounds were observable.

EXAMPLE 2

The process of Example 1 is repeated with the following changes: (a) Instead of the preparation of the ALV according to item (a) of Example 1, an ALV containing liquid was prepared by inoculating duck eggs which were previously brooded for 9 days with the passaged 127 virus strain. After 7 days incubation at 37° C., the AAF (amnion allantoic fluid) was harvested and the AAF then had a HA titer of about 1:1024. The virus suspension was subsequently frozen at $-20°$ C. and stored for vaccine production.

(b) After treatment of the NDV suspension as described under (c) of Example 1, and inactivation of the ALV suspension with 0.02 to 0.5% formaldehyde for 20 hours at 22° C., the NDV- and the ALV-liquids were mixed in a ratio of 4:1 and used for the preparation of the emulsion as described under (d) of Example 1.

EXAMPLE 3

An ALV containing liquid was prepared as in Example 2 and an NDV containing liquid was prepared as in Example 1. The treatment of the NDV suspension was carried out in the same way as in Example 1 and the treatment of the ALV suspension was carried out as in Example 2. The treated NDV-AAF and ALV-AAF were mixed thereafter in a proportion of 5:1.

The combined virus suspensions were added to and mixed with an oil phase in the proportion of 6.5 parts of oil phase: 3.5 parts of virus containing liquid and an emulsion was prepared by passing it through a colloid mill. The oil phase had the following composition: 91.4 vol% of Marcol 52, 8.0 vol% of Arlacel A or Arlacel 80 or Span 80 and 0.6 vol% of Tween 80.

EXAMPLE 4

An ALV containing liquid and a NDV containing liquid were prepared according to the respective steps of Example 1. After treatment of the virus suspensions as in Example 1, the NDV-AAF and the ALV containing liquid were mixed in a proportion of 4:3 and an emulsion was prepared in the same way as in Example 1. However, the oil phase and the combined virus containing liquids were mixed in a proportion of 6:4, while the oil phase was that used in Example 1.

EXAMPLE 5

The combined vaccine prepared in Example 4 was tested in the following way.

Not previously vaccinated 8 weeks old SPF chickens were vaccinated with the combined vaccine. The found HAI (hemagglutinating inhibition)-titers and the number of HAI-units respectively in the sera coming from the vaccinated animals did not significantly deviate from the antibody levels, found in animals which were vaccinated with the corresponding single vaccines of a comparable composition under the same conditions.

The progress curves obtained by plotting the found HAI-units and HAI-levels respectively expressed in the form of $2^x$ on a logarithmic scale against the time is shown in FIG. 1.

As to the NDV-HAI-units, significantly higher values were found with animals which had previously been vaccinated before with live NDV vaccine (as is usually done in the field). By such animals e.g. about $10^{16.0} - 10^{17.0}$ NDV-HAI-units were detected in the period of 4 to 8 weeks after vaccination with the combined NDV-ALV vaccine.

Various modifications of the products and processes of the invention may be made without departing from the spirit or scope thereof and it is to be understood that the invention is to be limited only as defined in the appended claims.

We claim:

1. In a combined inactivated vaccine ready for administration and active against Newcastle disease and egg production drop comprising a mixture of an aqueous phase containing an inactivated adeno-like virus (ALV) and an inactivated Newcastle disease virus (NDV) and an oily phase containing at least one emulsifier, the improvement, resulting in a smaller volume for administration, thus causing less irritation, comprising the aqueous phase comprising an adeno-like virus (ALV) containing aqueous liquid obtained by cultivating an in duck egg passaged virus strain 127 with a titre of at least $4 \times 10^2$ units/ml and an aqueous liquid of an inactivated Newcastle disease virus (NDV) with a titre of at least $10^{9.8}$ EID$_{50}$/ml, the volume ratio of NDV-liquid and ALV liquid being 3:4 to 5:1 and the volume ratio between the aqueous phase containing both virus liquids and the oily phase being 7:13 to 3:7.

2. The vaccine of claim 1 wherein the oily phase is comprised of at least one compound selected from the group consisting of light paraffinic mineral oil, vegetable oil and naphthenic mineral oil and at least one emulsifier selected from the group consisting of ester-ethers and esters derived from at least one component selected from the group consisting of alkylene oxide adducts, hexahydric alcohols and fatty acids of 10 to 20 carbon atoms.

3. An inactivated vaccine of claim 1 wherein the ALV liquid is an ALV-AAL liquid of duck's eggs and the volume ratio of NDV-liquid to ALV liquid is 3:1.

4. An inactivated vaccine of claim 1 or 3 wherein the NDV liquid is obtained by cultivation of Newcastle disease virus strains L/Z 258P deposited at Collection d' Institut Pasteur of Paris under No. I.091.

5. An inactivated vaccine of claim 1 wherein the NDV liquid has a titre of $\geq 10^{10}$ EID$_{50}$/ml.

6. The vaccine of claim 1 wherein the ratio is about 3:2.

7. The vaccine of claim 1 wherein the oil phase contains 2 to 20% by weight of at least one emulsifier.

8. The vaccine of claim 7 wherein the emulsifier is 0.2 to 4% of Tween 80 and 2 to 15% by weight of a member of the group consisting of Arlacel 80, Arlacel A and Span 80.

9. The vaccine of claim 1 wherein the ratio is about 7:13.

10. A method of immunizing chickens against Newcastle disease virus and egg production drops comprising simultaneously administering to chicken an immunizing effective amount of a composition of claim 1.

11. The method of claim 10 wherein the ratio is about 3:2.

12. The method of claim 10 wherein the oil phase contains 2 to 20% by weight of at least one emulsifier.

13. The method of claim 12 wherein the emulsifier is 0.2 to 4% of Tween 80 and 2 to 15% by weight of a member of the group consisting of Arlacel 80, Arlacel A and Span 80.

14. The method of claim 10 wherein the ratio is about 7:13.

* * * * *

UNITED STATES PATENT AND TRADEMARK OFFICE
CERTIFICATE OF CORRECTION

PATENT NO. : 4,537,768
DATED : Aug. 27, 1985
INVENTOR(S) : Peter Apontonweil and Johannes A.G. Kok It is certified that error appears in the above-identified patent and that said Letters Patent is hereby corrected as shown below:

Col.   Line 4      11        "√⁻¹"        should be -- √ --

4      67        "  "  "  "  "  "  "  "  "  "

5      46        "abovementioned" should be --above-mentioned--

8      Claim 5   "√⁻"         should be --√--

Signed and Sealed this

Eleventh Day of March 1986

[SEAL]

Attest:

DONALD J. QUIGG

Attesting Officer    Commissioner of Patents and Trademarks

UNITED STATES PATENT AND TRADEMARK OFFICE
CERTIFICATE OF CORRECTION

PATENT NO. : 4,537,768

DATED : August 27, 1985

INVENTOR(S) : Peter Apontonweil et al.

It is certified that error appears in the above-identified patent and that said Letters Patent is hereby corrected as shown below:

On the title page assignee should read:

-- (73) Assignee: Gist-Brocades N.V. Delft, The Netherlands --.

Signed and Sealed this

Tenth Day of June 1986

[SEAL]

Attest:

DONALD J. QUIGG

Attesting Officer

Commissioner of Patents and Trademarks